United States Patent [19]

Horrobin

[11] Patent Number: 4,931,468

[45] Date of Patent: Jun. 5, 1990

[54] PHARMACEUTICAL AND DIETARY COMPOSITION

[75] Inventor: David F. Horrobin, Montreal, Canada

[73] Assignee: Efamol Limited, Surrey, United Kingdom

[21] Appl. No.: 642,699

[22] Filed: Aug. 21, 1984

Related U.S. Application Data

[63] Continuation of Ser. No. 285,470, Jul. 21, 1981, abandoned, which is a continuation-in-part of Ser. No. 29,058, Apr. 11, 1979, Pat. No. 4,309,415.

[30] Foreign Application Priority Data

Apr. 11, 1978 [GB] United Kingdom ............... 14172/78
Sep. 4, 1978 [GB] United Kingdom ............... 35437/78

[51] Int. Cl.$^5$ .............................................. A61K 31/20
[52] U.S. Cl. ................................................... 514/560
[58] Field of Search ........................................ 514/560

[56] References Cited

PUBLICATIONS

Dyer, An Index of Tumor Chemotherapy, Mar., 1949, WIH, pp. 10–12 and 71.

*Primary Examiner*—Jerome D. Goldberg
*Attorney, Agent, or Firm*—Nixon & Vanderhye

[57] ABSTRACT

Use of γ-linolenic acid and related materials with (i) zinc, β-lactam antibiotics or other materials enhancing physiological 1-series PG synthesis and/or (ii) colchicine, Vinca alkaloids or other materials enhancing physiological synthesis of thromboxane A2, for treatment of malignant tumors susceptible to treatment with gamma-linolenic acid or dihomo-gamma-linolenic acid.

3 Claims, No Drawings

PHARMACEUTICAL AND DIETARY COMPOSITION

CROSS-REFERENCE TO RELATED APPLICATION

This application is a continuation of application Ser. No. 285,470, filed July 21, 1981, now abandoned, which is a continuation-in-part of my earlier application Ser. No. 029,058, filed Apr. 11, 1979, now U.S. Pat. No. 4,309,415.

FIELD OF THE INVENTION

This invention relates to the treatment of certain diseases and disorders primarily, but not exclusively, in the field of human medicine and to compositions for use therein.

GENERAL BACKGROUND

Considerable interest has been shown in recent years in the use of prostaglandin (PG) precursors in medicine.

For various reasons it is not practical to administer naturally-occurring prostaglandins such as PGE 1 and PGE 2 to patients. Consequently, considerable attention has focussed on the use of prostaglandin precursors including linoleic acid, γ-linolenic acid (GLA) and dihomo-γ-linolenic acid (DGLA).

Conversion of these materials in the body is believed to be as shown in the following diagram:

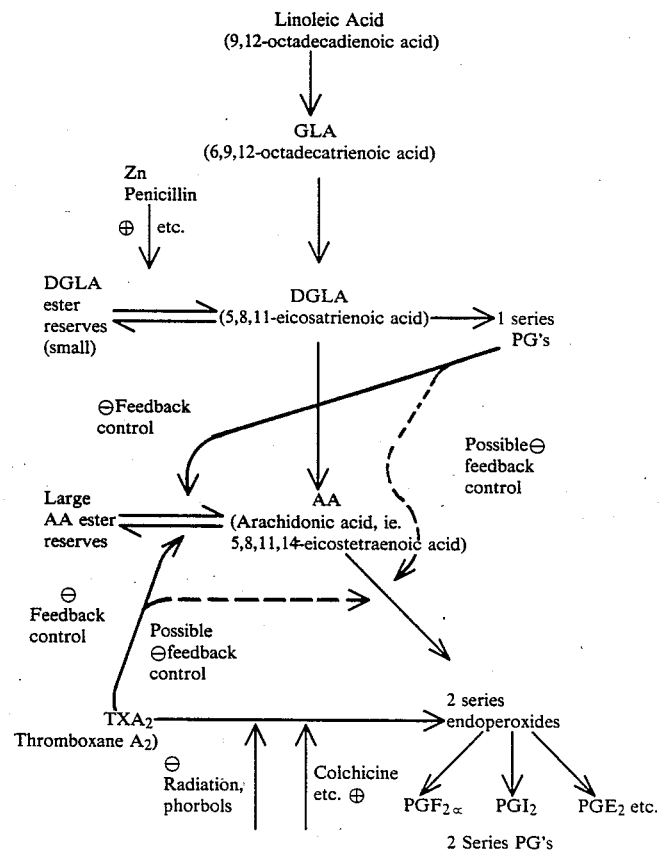

The broad outline of this pathway is well known, but the details of control, inhibition and enhancement are shown as the present inventor believes them to operate. The pathway is now discussed with particular reference to treatment of malignant tumors susceptible to treatment with gamma-linolenic acid or dihomo-gamma-linolenic acid according to the invention. This discussion is given in the belief that it elucidates the invention, but it is not intended that the invention should be limited by what is believed to be the reason for its effectiveness.

A major function of essential fatty acids (EFAs) is to act as precursors for prostaglandins (PGs), 1 series PGs being formed from dihomo-γ-linolenic acid (DGLA) and 2 series PGs from arachidonic acid (AA). DGLA and AA are present in food in only small quantities, and the major EFA in food is linoleic acid which is first converted to γ-linolenic acid (GLA) and to DGLA and AA. The conversion of linoleic acid to GLA is blocked by a high fat and high carbohydrate diet, by ageing and by diabetes. Stores of AA in the body in the form of lipid esters are very large indeed. In contrast only small amounts of DGLA ester are present.

There is evidence to show that in cancers, there is an overproduction of prostaglandins, abnormal calcium levels and a switch from an oxidative mode of metabolism to a glycolytic mode, which the present inventor believes may be due in part to a defect in the synthesis of TXA2. Such a defect may be caused for example by radiation. Moreover it is also believed that in an organism TXA2 binds to chromosomes and thereby increases their resistance to mutagens.

Thus, it is suggested, cancer involves two mechanisms, firstly a reduction in TAX2 levels and secondly an exposure to a mutagenic agent which leads to uncontrolled growth.

Therefore, many of the problems of cancer may be caused by the primary failure of TXA2 synthesis and the secondary excess of prostaglandins of the 2 series and depletion of prostaglandins of the 1 series and essential fatty acids.

Thus the invention, in one aspect, serves to redress the 1-series PG depletion by administering γ-linolenic acid and/or other materials tending to enhance 1-series PG production. In another aspect, desirably combined with the first, it seeks to restore TXA2 production directly.

It has further recently been found that a critical factor in some inflammatory disorders, e.g. in the damage of myelin which occurs in multiple sclerosis, may be the entry of calcium into cells. This may damage mitochondria and activate destructive lysosomal enzymes. Thus, there is now evidence which indicates that the regulation of the immune response and also the control of intracellular calcium may be significant factors in the treatment of various inflammatory disorders.

The present inventor has now found that colchicine is a substance which appears to be able to potentiate the removal of calcium by cells and thus may be able to control intracellular calcium. Colchicine may also inhibit formation of 2 series PG's and enhance formation of 1 series PG's. In a further aspect of the invention, therefore, in conjunction with correction in EFA balance, colchicine is administered to effect such control. The relationship of this to EFA metabolism is discussed later.

In cancers as discussed above, and in inflammatory disorders, production of 2 series PGs from arachidonic acid is greatly exaggerated. In inflammatory disorders these PGs are thought to contribute to the causation of the disease because steroids and aspirin-like drugs are both partially effective therapies, steroids blocking the conversion of AA esters to free AA and aspirin-like drugs blocking the conversion of free AA to endoperoxides which are intermediates in PG synthesis. As yet there is less evidence that the increased formation of 2 series PGs plays an important part in cancer but some human tumours are known to respond to steroids and growth of some animal tumours is inhibited by aspirin-like drugs.

The overproduction of 2 series PGs implies that normal control of the PG synthetic pathway has been lost. Although control of this pathway is imperfectly understood two factors have been identified.

1. PGE1 is able to inhibit the formation of free AA from AA esters. This leads to the paradoxical fact that a partial EFA deficiency actually leads to increased formation of 2 series PGs, because DGLA stores are so much smaller than those of AA and a partial deficiency of EFAs will therefore lead to DGLA depletion first. This depletion will reduce formation of PGE1, remove the PGE1 control of AA and allow overproduction of 2 series PGs from the large AA stores.

2. An unstable product of AA metabolism, thromboxane A2 (TXA2), also feeds back to inhibit conversion of AA ester to free AA and possibly also of free AA to PG2 endoperoxides. Thus loss of TXA2 will also lead to overproduction of 2 series PGs. TXA2 and PGE1 thus cooperate in the regulation of formation of 2 series PGs and a fault in the formation of either will lead to abnormalities.

Thus for example the disorders of PG synthesis in inflammatory disorders can be accounted for by inadequate formation of PGE1 and/or TXA2.

The evidence for direct involvement of PGs in inflammatory disorders and cancer has been briefly mentioned. There is also indirect evidence that PGs may act by regulating—or failing to regulate—the calcium movements into and out of cells already mentioned above. The calcium concentration in cytoplasm is normally very low and there is now excellent evidence from many sources that a brief rise in cytoplasmic calcium concentration triggers a variety of cell events, including cell division and activation of lysosomes which contain destructive enzymes. Normally this calcium is very rapidly removed after this brief activation so terminating the event. PGs and related substances have specific actions on calcium and the present inventor has obtained evidence to suggest that TXA2 and PGF2α may be of critical importance. In particular, specific inhibition of TXA2 synthesis greatly prolongs the time taken for calcium to be removed from the cytoplasm after activation. Furthermore, inhibition of TXA2 synthesis leads to increased formation of PGF2α and PGE2 which can promote calcium entry into cells. There is thus good evidence that in this respect also PGE1 and TXA2 enhance one another's effects. In particular, in muscle the degree of contraction is related to the calcium concentration in the cytoplasm and muscle contraction is a measure of this calcium concentration. After inhibition of TXA2 synthesis the recovery from a contraction is greatly prolonged indicating slow removal of calcium. Further, inhibition of TXA2 synthesis can lead to a chronic state of partial contraction indicating the entry of calcium into the cytoplasm. PGF2α and PGE2 whose output is increased by inhibition of TXA2 synthesis also cause contraction indicating calcium entry into the cytoplasm.

Thus loss of TXA2 and PGE1 synthesis will lead to increased formation of 2 series PGs and entry of calcium into the cytoplasm. This calcium may activate cell division and also activate lysosomes whose destructive enzymes may play a large part in inflammation.

There is a good deal of evidence that cancers do indeed not produce TXA2 normally. The most striking is as follows:

(a) Specific inhibitors of TXA2 synthesis, such as imidazole, can produce in normal cells biochemical abnormalities similar to those in naturally occurring cancers.

(b) Radiation and phorbol esters, which powerfully promote the development of cancers, are both able to inhibit the enzyme which forms TXA2.

The evidence of defective 1 series PG synthesis in cancer is less substantial at present. However, rapidly growing cancers frequently produce skin lesions in their hosts which are identical to those caused by 1 series PG deficiency. Further, in rat breast cancer there is evidence that synthesis of α-lactalbumin is regulated by PGE1, and α-lactalbumin synthesis fails as the breast tissue is transformed from the normal to the cancerous state.

There is suggestive evidence that TXA2 may be able to protect DNA from mutations. For example the phorbol esters do not cause mutations themselves but they do make cells much more susceptible to other mutagenic agents, or more particularly, the expression of their effect. It is possible that even when a mutation has taken place, it may not be expressed if adequate amounts of TXA2 are present. For example rats can be exposed to mutagenic radiation at birth but develop cancers only on administration of phorbol esters up to a year later.

On general ground there are therefore reasons to suppose that suppression of excess production of 2 series PGs will have desirable effects in both inflammatory disorders and cancer. Currently available conventional methods of suppression are administration of steroids and aspirin-like drugs. However, while these may suppress overproduction of 2 series PGs they will exaggerate further any deficiencies in PGs of the 1 series and in TXA2, which may explain why they control symptoms and do not usually alter the long term course of the disease.

The present invention proposes a radically new approach which will control excess PG2 series production by restoring towards normal, or enhancing, the formation of either or both of 1 series PGs and TXA2.

The methods proposed for doing this are as follows:

1 series PGs

To increase the available supply of precursors of 1 series PGs by providing adequate amounts of GLA or DGLA which will bypass any metabolic block between LA and GLA. The GLA or DGLA may be either synthetic or found in natural products. The formation of 1 series PGs may be enhanced further by the adminstration of pharmacological agents with the GLA or DGLA. Agents which have this effect are listed later in the specification. They include penicillamine and levamisole which have both been used as anti-inflammatory agents in rheumatoid arthritis with a completely unknown mechanism of action.

TXA2

To enhance the formation of TXA2 by means of agents which specifically activate the enzyme which forms TXA2 from PG2 series endoperoxides. These agents also are listed later in the specification, and include colchicine and related compounds such as the Vinca alkaloids.

These latter should be used in much lower doses than those at present used in cancer therapy, since high doses may have the reverse effect of inhibiting TXA2 formation. One has the apparently paradoxical situation that colchicine and the Vinca alkaloids may attack cancer in one of two ways. Low doses, according to the invention, activate TXA2 synthesis, inhibit formation of other 2 series PGs and restore calcium regulation. They will therefore tend to normalise cancer cells. High doses on the other hand, as given in known treatments, seem to be toxic to the enzyme. They therefore eliminate any remaining TXA2 synthesis, further enhance formation of PGF2α and other 2 series PGs and kill the cells by increasing calcium entry to the toxic level the effect nevertheless being sufficiently selective for cancer cells, to be of value.

It may be remarked that radiation also has apparently paradoxical effects which are explained in the concept on which the invention is based. Sub-lethal irradiation of normal cells inactivates TXA2 synthesis, opening the way to the abnormalities seen in cancer. Irradiation of cells in which TXA2 synthesis is already defective kills the cells by overloading them with calcium, the effect therefore being selective to cancer cells.

Direct evidence of effectiveness in the treatment of malignant tumors susceptible to GLA or DGLA is given at the end of the specification.

THE PRESENT INVENTION

In the light of the general discussion above and the present inventor's earlier U.S. patent application Ser. No. 4,924 dated Jan. 19th, 1979, now U.S. Pat. No. 4,273,763, the present invention in its various aspects may be stated as:

A. A method of treating malignant tumors susceptible to treatment with GLA or DGLA in a patient which comprises administering to the patient an effective amount of γ-linolenic acid and/or dihomo-γ-linolenic acid, optionally in association with linoleic acid and if desired other fat acids, said acids being used, if desired, as physiologically functional derivatives thereof.

PACKS

If it is not desired to have compositions comprising active materials listed above, packs may be prepared comprising the materials presented for separate or part joint and part separate administration in the appropriate relative amounts, and such packs are within the purview of the invention.

DIETARY COMPOSITION

The invention is chiefly described in terms of pharmaceutical compositions, but it will be understood that the γ-linolenic and other acids, being in the nature of dietary supplements, could be incorporated in a dietary margarine or other foodstuffs; such foodstuffs, possibly containing other active materials and generally referred to in this description as dietary or pharmaceutical compositions, are within the purview of the invention and thus of the term pharmaceutical compositions, packs or the like used in the claims.

VETERINARY APPLICATIONS

It will be understood that where a disorder of a kind calling for treatment in animals arises, the invention while described primarily in terms of human medicine and treatment is equally applicable in the veterinary field.

AMOUNTS OF ACTIVE MATERIALS

Amounts of zinc and β-lactam antibiotics are given later in general discussion of those materials.

Amounts of the alternative materials penicillamine, phenformin and levamisole are

| Penicillamine | 50 mg to 10 g/day |
|---|---|
| Phenformin | 10 mg to 5 g/day |
| Levamisole | 10 mg to 2 g/day |

For cancer the administration of colchicine, vinblastine, vincristine, griseofulvin, interferon or amantadine may conveniently be in the following amounts.

| Colchicine | 0.5 to 10 mg/day |
|---|---|
| amantadine | 100 to 1000 mg/day |
| griseofulvin | 0.5 to 5 g/day |
| Vinblastine | 0.5 to 5 mg/kg/week (average weight 70 kg) |
| vincristine | 0.1 to 1.0 mg/kg/week (average weight 70 kg) |
| interferon (by injection) | $1 \times 10^5$ to $1 \times 10^8$ units/day |
| melatonin | 10 mg to 5 g/day |

AMOUNTS OF γ-LINOLENIC AND OTHER ACIDS SPECIFICALLY

A preferred daily dosage for an adult (weight ca 75 kg) is from 0.05 or 0.1 up to 1, 2, 5 or even 10 g as required of γ-linolenic acid or equivalent weight (calculated as γ-linolenic acid) or physiologically functional derivative thereof. Amounts may in particular be 0.1 to 1.0 g daily. Such doses correspond to about 2 to 20 g daily of the Oenothera oil discussed below. In place of, or in addition to, γ-linolenic acid, one may use dihomo-γ-linolenic acid or a physiologically functional derivative thereof, in amounts equivalent in molar terms to γ-linolenic acid and calculated as such. This dosage can for example be taken as a single dose or divided into 2, 3 or 4 subdivisions thereof as convenient.

Based on present evidence, a particularly suitable daily dosage in the treatment of malignant tumors susceptible to treatment with GLA or DGLA for an adult (weight ca 75 kg) would be from 0.15 to 1.5 g of γ-linolenic acid or equivalent weight of functional derivative thereof.

FORMS AND SOURCES OF γ-LINOLENIC AND OTHER ACIDS

Convenient physiologically functional derivatives of γ-linolenic acid and dihomo-γ-linolenic acid for use according to the invention for all the purposes described include the $C_1$–$C_4$ alkyl (e.g. methyl and ethyl) esters and the glycerides of the acids.

If desired, pharmaceutical compositions may be produced for use in the invention by associating natural or synthetic γ-linolenic acid (or a physiologically functional derivative thereof) and/or dihomo-γ-linolenic acid (or a physiologically functional derivative thereof) as such, with an acceptable pharmaceutical vehicle. It is at present convenient to incorporate the γ-linolenic acid into compositions in the form of an available oil having a high γ-linolenic acid content.

At the present time known natural sources of oils having a high γ-linolenic acid content are few (there are no known natural sources of significant amounts of dihomo-γ-linolenic acid). One source of oils currently available is the seed of Evening Primrose species such as *Oenothera biennis L.* and *Oenothera lamarckiana*, the oil extract therefrom containing γ-linolenic acid (about 8%) and linoleic acid (about 72%) in the form of their glycerides together with other glycerides (percentages based on total fatty acids). Another source of γ-linolenic acid is the seed of Borage species such as *Borago officinalis* which, though its current yield per acre is low, provides a richer source of γ-linolenic acid than Oenothera oil. Recent studies on fungi which can be cultivated by fermentation promise a fungal oil source.

The seed oil extracts referred to above can be used as such or can for example if desired be fractionated to yield an oily composition containing the triglycerides of γ-linolenic acid and linoleic acid as the main fatty acid components, the γ-linolenic acid content being if desired a major proportion. Seed oil extracts appear to have a stabilizing effect upon any dihomo-γ-linolenic acid or physiologically functional derivative thereof incorporated therein.

USE OF ZINC

Without restriction to the theory, it is believed that zinc tends to stimulate the biosynthesis of 1 series PG's and specifically that it potentiates mobilisation of esterified reserves of dihomo-γ-linolenic acid. This enables one to use zinc conjointly with γ-linolenic acid and/or dihomo-γ-linolenic acid. The presence of arachidonic acid or any other material tending to oppose the PG1 enhancing effect is, naturally to be avoided.

Based on present evidence, a suitable daily dosage for an adult (weight ca 75 kg) is 2.5–800 mg preferably 10–200 mg and advantageously 10–80 mg zinc daily, with γ-linolenic acid or other acid or equivalent in the amounts previously discussed. The 10–80 mg zinc is approximately 0.125–1.0 mg/kg adult body weight. In view of the conjoint effect of the zinc preferred amounts of γ-linolenic or other acid or equivalent are less than when zinc is not present, advantageously 0.1 to 1.0 g daily. As before the dosage can be taken as a single dose or divided into 2, 3 or 4 subdivisions thereof.

Conveniently the zinc and γ-linolenic or other acid or derivatives are given together in a single preparation but they can of course be taken separately.

The zinc should be administered in a form in which it is readily taken up in vivo. Ordinarily this will indicate the use of a zinc salt of a mineral or organic acid, said salt being physiologically acceptable at the given dosage. Some zinc salts which would be contraindicated at higher dosages may be satisfactory for present purposes at the dosages indicated above. Useful salts include zinc sulphate and zinc gluconate and in particular zinc oleate, γ-linolenate and dihomo-γ-linolenate, and zinc oxide may also be employed. It is also possible to administer the zinc in chelated form. In any event, the preferred amounts of zinc are as stated above (the quantities given being calculated as zinc metal). Zinc oleate may be made by the method disclosed in Monatschrift 42 287 (1921) and similar methods may be applied to make for example zinc γ-linolenate if desired.

EXPERIMENTAL WORK ON USE OF ZINC

In one group of experiments the test preparation was the isolated superior mesenteric vascular bed, taken from male rats as for example described in the Canadian J. Physiol Pharmacol 54:357, 1976. The perfusion flow rate was at a constant value between 3 to 4 ml/min., pressure 25 to 30 mm Hg, using Krebs bicarbonate buffer containing in nM 150 Na, 4.3 K, 1.0 Mg, 2.5 Ca, 1.7 phosphate, 25 bicarbonate and 11.1 glucose.

Prior to testing the basic vasoconstrictive effect of norepinephrine as the bitartrate, in successive 10 ng amounts was established, as the amplitude of a transient rise of about 1 min. in the perfusion pressure.

Zinc, as the chloride, was then added to the perfusion buffer at successive concentrations and the norepinephrine response measured after 15 minutes at each.

The following results were obtained.

| Zinc concentration (μg/ml) | Response as % of basic level |
| --- | --- |
| 0.1 | 112 |
| 0.2 | 118 |
| 0.4 | 130 |
| 0.8 | 138 |

In the presence of 50 μg/ml of indomethacin, a known blocking agent for PG synthesis, used with 10 ng/ml PGE2 to give apparently normal vascular reactivity, the zinc had no effect on the norepinephrine response.

Similar tests with dihomo-γ-linolenic acid and PGE1 gave respective rises up to a maximum of 130% of the basic response at 50 ng/ml of the acid and a maximum of 150% of the basis response at $2.8 \times 10^{-11}$ M PG.

The results show that zinc gives responses like those of dihomo-γ-linolenic acid and of PGE1, responses moreover which are not given when PG synthesis is blocked and PGE2 supplied, and thus the conditions treated with γ-linolenic acid (and thus effectively with dihomo-γ-linolenic acid) may be enhanced in the direction of 1 series PG synthesis by the addition of zinc.

Analogous experiments with the same preparation show that phenformin, levamisole, penicillin and penicillamine have actions consistent with stimulation of PGE1 synthesis.

USE OF ZINC WITH OTHER MATERIALS

As shown above, in the perfused mesenteric vascular bed of the rat, zinc appears to increase the formation of PGE1 from DGLA. The presence of either colchicine (100 ng/ml) or melatonin (10 ng/ml) in the perfusion fluid increases the effect of zinc on PGE1 by 10 to 100 times, the size of the effect depending on the time of the year and being greater in the summer months than in the winter. This is probably because the production of melatonin from the pineal gland is lower in the summer than in the winter and the effect of extra melatonin can therefore be more easily seen in the summer. Colchicine and melatonin appear to act at the same sites in cells, and their overall effect therefore is to increase the formation of PGE1. The effect is believed to be mediated at least in part by the effect of colchicine and melatonin on thromboxane A2. The alternative materials to colchicine previously mentioned may be expected to have similar effects.

USE OF ε-LACTAM ANTIBIOTICS

ε-lactam antibiotics which may be used according to the present invention, are conveniently any of the known penicillin and cephalosporin antibiotics (including semi-synthetic antibiotics) such as, for example, penicillin G, penicillin N, penicillin V, cephalexin, cephalothin, ampicillin, amoxycillin, cloxacillin and cephaloglycin. Any of these may be used in the form of their physiologically functional non-toxic derivatives, for example alkali metal salts e.g. sodium and potassium salts, and salts with organic bases, and reference to an antibiotic herein (including the claims) includes reference to such derivatives.

Suitable daily dosages may for example be in the range 0.5 to 10.0 g per day in patients of average weight. Such daily dosages may conveniently be divided as for zinc.

The use of penicillins in long term treatments is especially desirable in view of the known relative absence of side effects of : these drugs. Thus, penicillin has been administered for many years to patients having rheumatic heart disease in order to prevent streptococcal infections, and there is virtually no evidence of long term toxicity.

Care should of course be taken to ensure that the patient is not allergic to the drug of choice.

It is believed that the reason for the effectiveness of the antibiotics in certain disorders is that they enhance utilisation of ester reserves of dihomo-γ-linolenic acid. Whether or not this is so, and no restriction to the theory is intended, zinc and antibiotics do appear to have parallel effects in treating all the conditions discussed herein when used with the γ-linolenic or other acids and derivatives.

In particular in tests carried out on the rat mesenteric bed system as above, both penicillin V and penicillin G have given responses similar in kind and degree to those given for zinc, supporting further inventor's belief that β-lactam antibiotics are of value in all other conditions treated according to the invention in similar way to the action of zinc. It may be expected that colchicine will enhance the effect of antibiotics just as it enhances the zinc effect.

PHARMACEUTICAL PRESENTATION

The compositions according to the invention are conveniently in a form suitable for oral, rectal, parenteral or topical administration in a suitable pharmaceutical vehicle, as discussed in detail for example in U.K. Patent Specification No. 1 082 624 and in any case very well known generally for any particular kind of preparation. Thus for example tablets, capsules, ingestible liquid or powder preparations, creams and lotions for topical application, or suppositories, can be prepared as required. Injectable solutions of hydrolysed Oenothera oil may be prepared using albumin to solubilise the free acid.

Advantageously a preservative is incorporated into the preparations. α-Tocopherol in a concentration of about 0.1% by weight has been found suitable for the purpose.

It will be understood that the absolute quantity of active ingredients present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired.

The following Examples serve to illustrate pharmaceutical compositions useful in treatment according to the invention:

EXAMPLES

Pharmaceutical compositions containing a unit dose of an oil extract from the seeds of *Oenothera biennis* L. optionally with methyl dihomo-γ-linolenate and/or zinc sulphate and/or penicillin V and/or any of the other active materials referred to herein are prepared by encapsulation of the natural oil in soft gelatin capsules manufactured by known methods.

The oil is extracted from the seeds by one of the conventional methods of extraction such as cold pressure, screw pressure after partially cooking the seed, or solvent extraction.

Fractionation of a typical sample of this oil shows a yield of 97.0% oil in the form of methyl esters, with the relative proportions.

| Palmitate | 6.15 |
| Stearate | 1.6 |
| Oleate | 10.15 |
| Linoleate | 72.6 |
| γ-Linolenate | 8.9 |

As preservative, o-tocopherol is added to the oil in a concentration of 0.1%.

Gelatin capsules containing oil extracts prepared as described above, each having the following contents of active ingredients (0.5 g oil extract=ca 0.045 g γ-linolenic acid), are prepared in conventional fashion.

EXAMPLE 1

| Oil extract | 0.5 g |
| Zinc sulphate | 10 mg |

Two capsules may be administered thrice daily in the treatment of susceptible malignant tumors as above, giving a daily dose of γ-linolenic acid of ca 0.27 g. Capsules without zinc are an alternative.

EXAMPLE 2

| | |
|---|---|
| Oil extract | 0.5 g |
| Methyl dihomo-γ-linolenate | 10 mg |
| Zinc sulphate | 20 mg |

Two capsules may be administered thrice daily in the treatment of susceptible malignant tumors as above.

EXAMPLE 3

| | |
|---|---|
| Oil extract | 0.5 g |
| Penicillin V | 0.25 g |

Two capsules may be administered thrice daily in the treatment of susceptible malignant tumors as above. Levamisole 25 mg, penicillamine 100 mg or phenformin 25 mg are alternatives to penicillin.

EXAMPLE 4

| | |
|---|---|
| Oil extract | 0.5 g |
| Penicillin V | 0.25 g |
| Zinc sulphate | 10 mg |

Two capsules may be administered thrice daily in the treatment of susceptible malignant tumors as above. Levamisole 25 mg, penicillamine 100 mg or phenformin 25 mg are alternatives to penicillin.

EXAMPLE 5

| | |
|---|---|
| Oil extract | 0.5 g |
| Methyl dihomo-γ-linolenate | 10 mg |
| Penicillin V | 0.25 g |
| Zinc sulphate | 10 mg |

Two capsules may be administered thrice daily in the treatment of susceptible malignant tumors as above.

EXAMPLE 6

| | |
|---|---|
| Oil extract | 0.5 g |
| Methyl dihomo-γ-linolenate | 10 mg |

Two capsules may be administered twice daily in the treatment of susceptible malignant tumors as above.

EXAMPLE 7

| | |
|---|---|
| Oil extract | 0.5 g |
| Colchicine | 0.15 mg |

One capsule may be administered four times daily in the treatment of susceptible malignant tumors as described above.

EXAMPLE 8

| | |
|---|---|
| Oil extract | 0.5 g |
| Methyl dihomo-γ-linolenate | 10 mg |
| Colchicine | 0.3 mg |

One capsule may be administered four times daily in the treatment of susceptible malignant tumors as described above.

EXAMPLE 9

| | |
|---|---|
| Oil extract | 0.5 g |
| Colchicine | 0.25 mg |
| Penicillin V | 0.25 g |

One or two capsules may be administered four times daily in the treatment of susceptible malignant tumors as described above.

EXAMPLE 10

| | |
|---|---|
| Oil extract | 0.5 g |
| Colchicine | 0.25 mg |
| Zinc oleate | 20 mg |

One or two capsules may be administered four times daily in the treatment of susceptible malignant tumors as described above.

EXAMPLE 11

| | |
|---|---|
| Oil extract | 0.5 g |
| Phenformin | 25 mg |
| Amantadine | 100 mg |

One or two capsules may be administered four times daily in the treatment of susceptible malignant tumors as described above.

EXAMPLE 12

| | |
|---|---|
| Oil extract | 0.5 g |
| Colchicine | 0.25 mg |
| Levamisole | 25 mg |

One or two capsules may be administered four times daily in the treatment of susceptible malignant tumors as described above.

EXAMPLE 13

| | |
|---|---|
| Oil extract | 0.5 g |
| Colchicine | 0.25 mg |
| Penicillamine | 100 mg |

One or two capsules may be administered four times daily in the treatment of susceptible malignant tumors as described above.

EXAMPLE 14

| | |
|---|---|
| Oil extract | 0.5 g |
| Griseofulvin | 0.5 mg |

One capsule may be administered four times daily in the treatment of susceptible malignant tumors as described above.

EXAMPLE 15

Oil extract capsules or oil extract plus zinc capsules may be administered as in Example 1 in conjunction with 70 mg/week vinblastine.

EXAMPLE 16

Oil extract capsules or oil extract plus zinc capsules may be administered as in Example 1 in conjunction with 70 mg/week vincristine.

EXAMPLE 17

Oil extract capsules or oil extract plus zinc capsules may be administered as in Example 1 in conjunction with 0.5 g/day melatonin.

EXAMPLE 18

Oil extract capsules or oil extract plus zinc capsules may be administered as in Example 1 in conjunction with $1 \times 10^6$ units day/interferon.

Cancer trials in humans inevitably take several years but the present inventor has shown the potential value of the approach in the R3230AC rat mammary cancer. Administration of Evening Primrose oil can reduce the rate of growth of established cancers to less than half. Colchicine and melatonin have similar effects and the combination of oil and colchicine, melatonin or other materials listed with them in the specification will be even more desirable. These cancers are started by transplantation of minute pieces of tumour tissue, and normally over 90% of these tumours "take" and grow, but if Evening Primrose oil is administered before and immediately after transplantation, less than 40% of the transplants develop into full tumours.

Specially, 1 mm diameter pieces of the transplantable R3230AC breast tumour were transplanted subcutaneously in rats of the Fisher strain (50 animals). After five weeks the animals were killed and the tumours removed. In 10 control animals which received daily saline injections the mean tumour weight was 1.6 gram. In 10 animals which received 25 microliters of Evening Primrose oil subcutaneously each day the mean tumour weight was 0.64 g. In 10 animals which received 100 microliters of Evening Primrose oil daily mean tumour weight was 0.46 g. In 10 animals which received 25 microliters oil plus 10 microg colchicine per day mean tumour weight was 0.32 g. In 10 animals which received 25 microliters oil plus 1 mg penicillin G per day the mean tumour weight was 0.36 g. The treatments thus substantially slowed tumour growth.

In view of these results a larger series was undertaken.

BACKGROUND

Prolactin may stimulate either proliferation and growth or lactogenesis in mammary tissue. It may also either enhance or inhibit growth of mammary tumours and has numerous actions at the second messenger level. It has been proposed that one of these actions, the enhancement of prostaglandin E1 synthesis, is the key determinant of the pattern of prolactin action. The suggestion is that low PGE1 levels will enhance proliferation and tumour growth while high PGE1 levels will enhance lactogenesis and inhibit tumour growth. Increasing PGE1 production by any mechanism should therefore inhibit the growth of mammary tumours.

PGE1 is unstable and rapidly destroyed and so is difficult to use experimentally. In these experiments we have therefore used Evening Primrose oil (72% cis-linoleic acid, 9% γ-linolenic acid, 19% other fatty acids), the richest available source of the essential fatty acid precursors of PGE1.

METHODS

Small uniform sized pieces of the R3230AC mammary tumour were transplanted subcutaneously into female Fisher rats weighing about 150 g. The animals were followed for six weeks, at the end of which they were killed and the tumours dissected out, measured and weighed. The animals were housed in five groups of ten animals each. The groups received the following treatments starting 2 days prior to tumour transplantation and continuing until the time of death. Injections were given subcutaneously each morning at a site remote from the tumour. 1. Control 200 μl olive oil daily (olive oil has a very low content of essential fatty acids). 2. 25 μl Evening Primrose oil daily. 3. 50 μl Evening Primrose oil daily. 4. 100 μl Evening Primrose oil daily. 5. 200 μl Evening Primrose oil daily.

RESULTS

The results are shown in Table 1. Each Figure represents the mean±SEM for 10 animals. The p values represent the differences from control. Statistical analysis was by Student's t test.

TABLE 1

Tumour size indicates the length × width in mm². Tumour weight is in g. The tumour wt/body wt ratio is the tumour wt × 100 divided by the body weight.

| Group | Tumour size | p < | Tumour wt | p < | Tumour/body | p < |
|---|---|---|---|---|---|---|
| Control | 286.3 ± 46.4 | | 5.05 ± 0.85 | | 3.62 ± 0.59 | |
| 25 μl EPO | 145.1 ± 43.4 | 0.01 | 2.44 ± 0.62 | 0.01 | 1.83 ± 0.43 | 0.01 |
| 50 μl EPO | 118.9 ± 18.8 | 0.01 | 1.97 ± 0.34 | 0.01 | 1.47 ± 0.24 | 0.01 |
| 100 μl EPO | 84.4 ± 22.3 | 0.001 | 1.62 ± 0.41 | 0.001 | 1.24 ± 0.30 | 0.001 |
| 200 μl EPO | 163.4 ± 25.9 | 0.05 | 3.08 ± 0.77 | 0.05 | 2.09 ± 0.62 | 0.01 |

DISCUSSION

In all four groups treated with Evening Primrose oil tumour sizes, tumour weights and tumour wt/body wt ratios were significantly less than in the control group. Maximum suppression was achieved with a dose of 100 μl per day, while 200 μl per day was consistently less effective than 25 μl/day. PGE1 has however repeatedly been observed to demonstrate biphasic or "bell-shaped" dose/response curves, with the effects of an absence and of an excess of PGE1 being similar.

In a short follow up experiment three groups of 10 rats were transplanted with R3230AC tumors and followed for 2 weeks after which they were sacrificed and the tumours weighed and measured. One group served as a control and the other two were treated with 100 μl primrose oil daily. One of the primrose oil groups received 4 mmol/kg lithium chloride intraperitoneally each day. After two weeks tumour wt in the primrose oil alone group was 52%±17% of control. In the primrose oil plus lithium group, tumour wt was 89%±19% of control. The lithium therefore largely blocked the primrose oil effect which, as lithium is known to have a selective effect in inhibiting conversion of essential fatty acids to PGE1, suggests the belief that the effect of the Evening Primrose oil was through PGE1.

Further, in one male human patient with an ultra-violet radiation induced basal cell carcinoma (rodent ulcer) of the face, administration of Evening Primrose oil (3 ml/day) caused complete disappearance of a 5 mm tumour within 6 weeks. The present inventor knows of no instance of spontaneous regression of this type of tumour.

Two further patients have also been treated. The first is a man who had been having treatment since 1965 for a histologically verified papillary bladder carcinoma. It had been controlled for some years by repeated cystodiathermy but by 1977 was getting out of control, involving the greater part of the bladder with heavy haematuria. Radical radiotherapy and monthly diathermy was used but by January 1979 the condition was considered beyond help by surgery, radiotherapy or conventional chemotherapy. In August 1979 10 g ascorbic acid was started daily but the tumour did not respond. In October 1979, Evening Primrose oil capsules, 0.5 g oil, eight daily, was started. Haematuria quickly improved and was absent by January 1980, with an accompanying feeling of well-being instead of the well-known unpleasant effects of chemotherapy and radiotherapy. The improvement had been maintained in review at December 1980.

The second patient is a woman who was seen in October 1979 and found by laparotomy to have both ovaries replaced by massive Krukenberg tumours. The whole abdomen was infiltrated by tumours shown on histology to be an anaplastic carcinoma of uncertain origin, possibly, with its primary site in the stomach. Vitamin C and Evening Primrose oil, 0.5 g daily and 8 capsules daily respectively as above, were started at once with early improvement in subjunctive well-being, erythrocyte sedimentation rate and bodily weight. By January 1980 the abdominal tumour masses were no longer detectable by palpation and ESR was down to 18 mm/hr from 76 mm/hr. The improvement had been maintained on review at December 1980, the case again being a "hopeless" case initially and in the opinion of experienced clinicians beyond the stage of help by conventional means.

Dosages in the claims hereafter are daily unless otherwise stated.

What is claimed is:

1. A method of treating malignant tumors sensitive to γ-linolenic acid or dihomo-γ-linolenic acid comprising administering to a person suffering therefrom an effective amount of γ-linolenic acid or physiologically functional derivative and/or dihomo-γ-linolenic acid or physiologically functional derivative thereof.

2. A method according to claim wherein the daily amount of said acid or derivative is 0.05 to 10 g calculated as γ-linolenic acid.

3. A method according to claim 2, wherein the daily amount of said acid or derivative is 0.1 to 5 g.

* * * * *